(12) United States Patent
Qi et al.

(10) Patent No.: US 9,221,724 B2
(45) Date of Patent: Dec. 29, 2015

(54) PROCESSES FOR PRODUCING LIGHT OLEFINS

(75) Inventors: Guozhen Qi, Shanghai (CN); Songyuan Gu, Shanghai (CN); Siqing Zhong, Shanghai (CN); Yongming Jin, Shanghai (CN)

(73) Assignees: China Petroleum & Chemical Corporation, Beijing (CN); Shanghai Research Institute of Petrochemical Technology, SINOPEC, Shanghai (CN)

( * ) Notice: Subject to any disclaimer, the term of this patent is extended or adjusted under 35 U.S.C. 154(b) by 1088 days.

(21) Appl. No.: 13/158,684

(22) Filed: Jun. 13, 2011

(65) Prior Publication Data

US 2011/0306811 A1    Dec. 15, 2011

(30) Foreign Application Priority Data

Jun. 11, 2010 (CN) .......................... 2010 1 0199796

(51) Int. Cl.
*C07C 1/20* (2006.01)
*B01J 29/90* (2006.01)
*B01J 38/34* (2006.01)

(52) U.S. Cl.
CPC . *C07C 1/20* (2013.01); *B01J 29/90* (2013.01); *B01J 38/34* (2013.01); *C07C 2529/85* (2013.01)

(58) Field of Classification Search
None
See application file for complete search history.

(56) References Cited

U.S. PATENT DOCUMENTS

| | | | |
|---|---|---|---|
| 4,171,286 A | 10/1979 | Dight et al. | |
| 4,370,222 A | 1/1983 | McGovern et al. | |
| 4,444,651 A | 4/1984 | Myers et al. | |
| 4,499,327 A | 2/1985 | Kaiser | |
| 4,849,091 A * | 7/1989 | Cabrera et al. | 208/113 |
| 5,447,622 A | 9/1995 | Kerby et al. | |
| 5,914,433 A * | 6/1999 | Marker | 585/313 |
| 6,166,282 A | 12/2000 | Miller | |
| 7,611,622 B2 * | 11/2009 | Niccum et al. | 208/78 |
| 2006/0025646 A1 | 2/2006 | Fung et al. | |
| 2007/0293709 A1 | 12/2007 | Iaccino et al. | |
| 2010/0179365 A1 | 7/2010 | Ito et al. | |
| 2010/0331596 A1 | 12/2010 | Xie et al. | |
| 2011/0218373 A1 | 9/2011 | Qi et al. | |

FOREIGN PATENT DOCUMENTS

| | | |
|---|---|---|
| CN | 1438296 | 8/2003 |
| CN | 1723262 | 1/2006 |

(Continued)

OTHER PUBLICATIONS

Li-Ping Ye et al., "Synthesis of SAPO-34 Molecular Sieves and Their Catalytic Performances in Methanol-to-Olefins Reaction," Journal of East China University of Science and Technology (Natural Science Edition) vol. 36, No. 1, pp. 6-12.

Non-final Office Action mailed Feb. 12, 2014, in co-pending U.S. Appl. No. 13/039,388.

(Continued)

*Primary Examiner* — In Suk Bullock
*Assistant Examiner* — Sharon Pregler
(74) *Attorney, Agent, or Firm* — Finnegan, Henderson, Farabow, Garrett & Dunner LLP

(57) ABSTRACT

A process for producing at least one light olefin, comprising converting three raw materials in the presence of at least one catalyst comprising at least one molecular sieve and regenerating said at least one catalyst into three separate product streams.

9 Claims, 1 Drawing Sheet

(56) References Cited

FOREIGN PATENT DOCUMENTS

| | | |
|---|---|---|
| CN | 101270023 | 9/2006 |
| CN | 101239869 | 8/2008 |
| CN | 101265150 | 9/2008 |
| CN | 101333141 | 12/2008 |
| CN | 101402538 | 4/2009 |
| CN | 101402539 | 4/2009 |
| WO | WO 2004/037950 | 5/2004 |
| WO | WO 2009/024012 A1 | 2/2009 |

OTHER PUBLICATIONS

Final Office Action mailed Jul. 15, 2013, in co-pending U.S. Appl. No. 13/039,388.
Non-final Office Action mailed Dec. 17, 2012, in co-pending U.S. Appl. No. 13/039,388.
Bishop, "Petroleum hydrocarbons and petroleum hydrocarbons measurements," May 1997, Massachusetts Department of Environmental Protection, Board of Registration of Hazardous Waste Site Cleanup Professionals.

* cited by examiner

PROCESSES FOR PRODUCING LIGHT OLEFINS

This application claims priority under 35 U.S.C. §119 to Chinese Patent Application No. 201010199796.X filed Jun. 11, 2010.

Disclosed herein are processes for producing at least one light olefin.

Light olefins, i.e., ethylene and propylene, are two important basic chemical materials with an increasing demand. Generally, ethylene and propylene are produced from petroleum. Due to limited supply and increasing price of petroleum resources, the cost of producing ethylene and propylene from petroleum resources is continuously increasing. Recently, techniques for preparing ethylene and propylene by conversion of petroleum alternatives have been developed. Oxygenates, such as alcohols (for example, methanol and ethanol), ethers (for example, dimethyl ether and methyl ethyl ether), esters (for example, dimethyl carbonate and methyl formate) and the like, can be converted to ethylene and propylene from petroleum alternatives such as coal, natural gas, biomass, and the like. Some oxygenates, such as methanol, can be produced from coal or natural gas on a large scale, reaching production scales of millions of tons. Due to the abundant supply of such oxygenates, in combination with the economically efficient technique of olefin production by conversion from petroleum alternatives, the Oxygenate To Olefins processes (OTO), such as the Methanol to Olefins processes (MTO), have drawn more and more attention. Examples of such processes are disclosed in U.S. Pat. Nos. 4,499,327 and 6,166,282, and CN1723262.

However, the yields of light olefins can be low using techniques known in the art. To improve economic efficiencies for manufacturing light olefins, the processes disclosed herein can produce at least one light olefin at high yield.

Specifically, disclosed herein is a process for producing at least one light olefin, comprising:
(1) providing a reaction-regeneration system comprising a primary reaction zone, a secondary reaction zone, and a regenerator,
wherein the secondary reaction zone comprises at least two risers; and further wherein the regenerator comprises at least two regeneration zones;
(2) transporting a first raw material comprising methanol, such as a first raw material comprising methanol with 99.5% of purity, into the primary reaction zone, wherein said first raw material is contacted with at least one catalyst comprising at least one molecular sieve, thus producing a product stream I, and also forming at least one coked catalyst;
(3) transporting the at least one coked catalyst to a first regeneration zone of the regenerator for regeneration to produce at least one regenerated catalyst, transporting a portion of the at least one regenerated catalyst into the second regeneration zone, and recycling another portion of the at least one regenerated catalyst to the primary reaction zone;
(4) transporting a portion of the at least one regenerated catalyst in the second regeneration zone into the first riser of the secondary reaction zone, wherein said at least one regenerated catalyst is contacted with a second raw material, thus producing a product stream II, transporting another portion of the at least one regenerated catalyst in the second regeneration zone into the second riser of the secondary reaction zone, wherein said at least one regenerated catalyst is contacted with a third raw material, thus producing a product stream III; and
(5) transporting both the product streams II and III and the at least one coked catalyst into a secondary disengaging zone for gas-solid separation, feeding the product streams II and III that have been subjected to said gas-solid separation into a separation section, and recycling the separated at least one coked catalyst to the first regeneration zone of the regenerator.

In some embodiments, the primary reaction zone as set forth above is a fast fluidized bed. In some embodiments, the at least one molecular sieve is selected from silicon-aluminophosphate molecular sieves chosen from SAPO-5, SAPO-11, SAPO-17, SAPO-18, SAPO-34, SAPO-35, SAPO-44, and SAPO-56. In one embodiment, the at least one molecular sieve is SAPO-34. In some embodiments, the second raw material comprises a mixed heavy hydrocarbon having a carbon number of 4 or more and an olefin mass content of more than about 60% by weight relative to the weight of the second raw material, and/or a mixed hydrocarbon having a carbon number of 4 or more obtained from said separation section. In some embodiments, the third raw material comprises a light hydrocarbon having an ethylene mass content of more than about 30% by weight relative to the total weight of the third raw material, and/or a light hydrocarbon obtained from said separation section. As disclosed herein, the term "light hydrocarbon" refers to hydrocarbons having a carbon number of less than 4. In one embodiment, a stripping section is arranged at the lower portion of said secondary disengaging zone. In some embodiments, the primary reaction zone has a reaction temperature ranging from about 400° C. to about 500° C., a gauge pressure ranging from about 0.01 to about 0.3 MPa, and a gas linear speed ranging from about 0.8 to about 2.0 m/s. In some embodiments, the first riser reactor has a reaction temperature ranging from about 510° C. to about 650° C., a gauge pressure ranging from about 0.01 to about 0.3 MPa, and a gas linear speed ranging from about 3.0 to about 10.0 m/s. In some embodiments, the second riser reactor has a reaction temperature ranging from about 500° C. to about 630° C., a gauge pressure ranging from about 0.01 to about 0.3 MPa, and a gas linear speed ranging from about 3.0 to about 10.0 m/s. In some embodiments, from about 50% to about 80% by weight of the at least one regenerated catalyst in the first regeneration zone is fed into the second regeneration zone, while from about 20% to about 50% by weight of the at least one regenerated catalyst in the first regeneration zone is recycled into the primary reaction zone. In some embodiments, the amount of carbon deposited amount on the catalyst fed into the first or second riser is less than about 0.5% by mass. In some embodiments, the amount of carbon deposited on the catalyst recycled from the first regeneration zone to the primary reaction zone ranges from about 0.5% and about 2.0% by mass. In some embodiments, from about 30% to about 70% by weight of the regenerated catalyst in the second regeneration zone is fed into the first riser reactor, while from about 30% to about 70% by weight of the regenerated catalyst in the second regeneration zone is fed into the second riser reactor.

The silicon-aluminophosphate (SAPO) molecular sieves used herein are prepared by a conventional method for person skilled in the art, for example, firstly preparing the molecular sieve precursor: mixing the following materials in a molar ratio of about 0.03~0.6 R:(about 0.01~0.98 Si:about 0.01~0.6 Al:about 0.01~0.6 P):about 2~500 H$_2$O, wherein R represents a templating agent, to form a mixed feedstock solution by crystallization at a certain temperature (e.g. from about 100° C. to about 250° C.), for a certain period of time (e.g. from about 1 hour to about 10 hours); secondly, hydrothermally crystallizing the resulting molecular sieve precursor at a temperature ranging from about 110° C. to about 260° C. for at least about 0.1 hours to obtain the SAPO molecular sieves. The resulting molecular sieves are mixed with at least one binder in a desired ratio, spray-dried, and calcined to obtain the SAPO catalyst, wherein the binder is generally in an amount ranging from about 10% to about 90% by weight of the molecular sieves. As disclosed herein, the feed for the primary reaction zone and first and second risers may be also added with a certain amount of at least one diluent selected, for example, from water vapor, while the weight ratio of the diluent to the feedstock is, for example, about 0-1:1.

It has been found that C4 olefin or ethylene may be used to generate light olefins such as propylene under certain conditions. In the process as disclosed herein, the system comprises a primary reaction zone and a secondary reaction zone. The primary reaction zone can, for example, be used for converting methanol to olefin, while the secondary reaction zone comprises a first riser and a second riser, wherein the first riser reactor can, for example, be used for the conversion of heavy hydrocarbons having more than 4 carbon atoms, and the second riser reactor can, for example, be used for the conversion of light hydrocarbons such as ethylene to enhance the yield of light olefins. Meanwhile, since methanol conversion has requirements different from those of heavy hydrocarbon or light hydrocarbon conversion, two grades of regeneration zones are used, wherein the first regeneration zone can, for example, be used for carrying out oxygen depleted regeneration to provide a catalyst with high selectivity and having a certain amount of carbon deposited thereon to the primary reaction zone, while the second regeneration zone can, for example, be used for carrying out the oxygen enriched regeneration to provide the secondary reaction zone with a catalyst having a higher activity. Moreover, the catalyst from the second regeneration zone generally can be active at a higher temperature, which is thus favorable for the conversion of hydrocarbons having more than 4 carbon atoms and ethylene to light olefins such as propylene. In addition, via the reaction in the secondary reaction zone, the coke burning amount of the regenerator may be increased, which can thus solve the problem of a lower coke yield in the primary reaction zone. Accordingly, the process disclosed herein can be used to both effectively enhance the yield of the target product light olefins and optimize energy utilization to achieve good economic efficiency.

In the reaction process of converting methanol into light olefins, a certain amount of carbon deposited on the catalyst is favorable for enhancing the selectivity of light olefins, and can, for example, range from about 1% to about 6% by weight relative to the total amount of the catalyst.

In some embodiments, in the product stream I, the yield of light olefins (carbon basis) reaches about 80.19% by weight, while in the product streams II and III, the yield of light olefins reaches about 41.25% by weight.

BRIEF DESCRIPTION OF THE DRAWINGS

In FIG. 1,
1 represents a feedstock inlet at the lower portion of a primary reaction zone;
2 represents the primary reaction zone;
3 represents a circulating sloped pipe;
4 represents an external cooler;
5 represents a pipe within the external cooler for recycling the gas to a disengaging zone;
6 represents a pipe for feeding the catalyst of the primary reaction zone to a first regeneration zone to be regenerated;
7 represents a pipe for conveying the catalyst from the first regeneration zone to the primary reaction zone;
8 represents a deposition section;
9 represents a gas-solid cyclone separator;
10 represents an outlet pipe of a product stream I;
11 represents a feedstock inlet of the second raw material;
12 represents a feedstock pipe of the stripping medium of the catalyst to be regenerated;
13 represents a first riser reactor;
14 represents a stripping section of the pipe for conveying the catalyst to be regenerated;
15 represents a conveying medium feedstock pipe for conveying the regenerated catalyst to a second riser reactor;
16 represents three gas-solid cyclone separators;
17 represents a feedstock inlet of a third raw material;
18 represents a first regeneration zone;
19 represents a regenerator;
20 represents a gas-solid cyclone separator;
21 represents an outlet pipe of the flue gas of the regenerator;
22 represents a medium feedstock pipe for conveying the regenerated catalyst to the first riser reactor;
23 represents a second riser reactor;
24 represents a stripping section;
25 represents a secondary disengaging zone;
26 represents an outlet pipe of product streams II and III;
27 represents an inlet pipe of stripping medium;
28 represents a sloped pipe for conveying material to be regenerated;
29 represents standing pipes for conveying the catalyst;
30 represents a second regeneration zone;
31 represents a feedstock pipe of the regeneration medium of the first regeneration zone 18; and
32 represents a feedstock pipe of the regeneration medium of the second regeneration zone 30.

Figure 1:
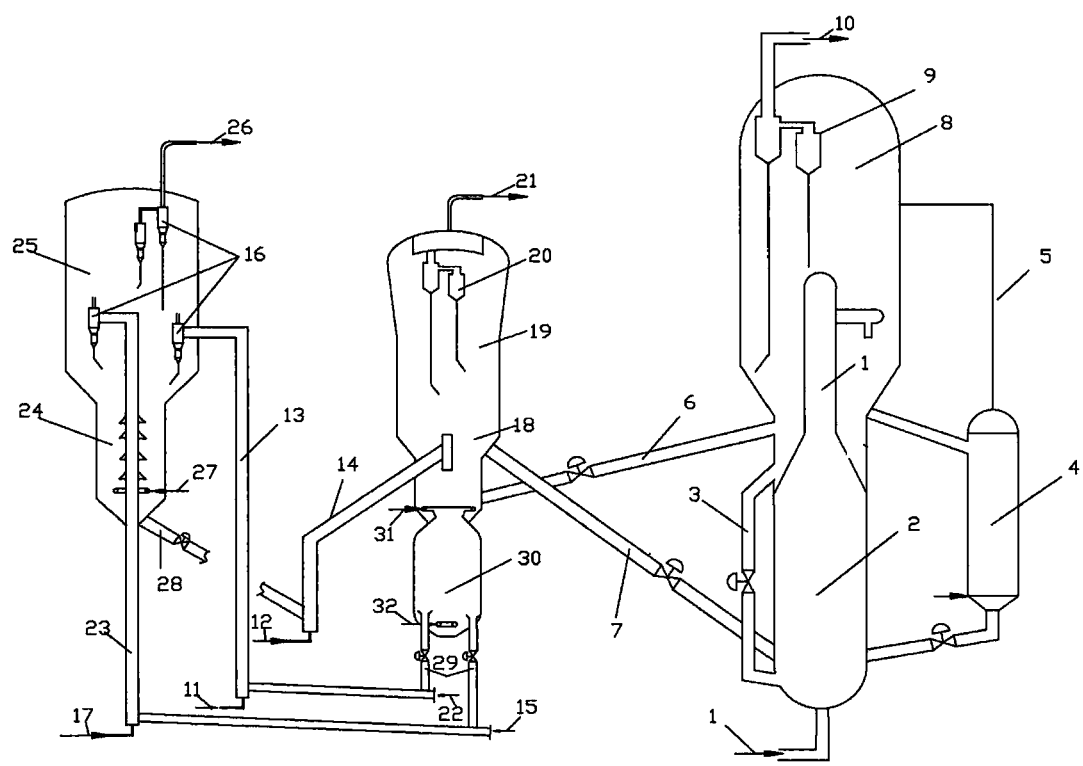
FIG. 1 is a representative schematic view of one embodiment of the process as disclosed herein.

The first raw material comprising methanol is fed into the primary reaction zone 2 to be contacted with at least one catalyst comprising at least one molecular sieve. A product stream I is generated. And also a coked catalyst is formed. The product stream I is separated by a gas-solid separator 9 and fed into the separation section via an outlet pipe 10. For the separated coked catalyst, one portion is recycled into the primary reaction zone 2 via a circulating sloped pipe 3; another portion is fed into the first regeneration zone 18 of the regenerator 19 for regeneration via a pipe 6. For the resulting regenerated catalyst, one portion is fed into the second regeneration zone 30, while another portion is recycled into the primary reaction zone 2. For the regenerated catalyst in the second regeneration zone 30, one portion is fed via a pipe 22 into the first riser 13 of the secondary reaction zone to be contacted with the second raw material from the pipe 11 and thus produce a product stream II; another portion is fed via a pipe 15 into the second riser 23 of the secondary reaction zone to be contacted with the third raw material from the pipe 17 and thus produce a product stream III. Both the product streams II and III, together with the catalyst, are passed to a secondary disengaging zone 25. The product streams II and III that have been subjected to gas-solid separation are fed into a separation section via a pipe 26. The separated catalyst is stripped via a stripping section 24 and then recycled to the first regeneration zone 18 of the regenerator.

The embodiments of the present disclosure described herein are representative and not limitative. Disclosed embodiments herein include the following non-limitative examples.

EXAMPLE 1

In the small-sized reaction-regeneration device as shown in FIG. 1, the primary reaction zone was a fast fluidized bed. The regenerator included two regeneration zones. The first regeneration zone was located above the second regeneration zone. The secondary reaction zone included two risers, wherein the upper portion of the first riser was located inside the secondary disengaging zone and stripping section; the second riser was located outside the secondary disengaging zone. The regeneration medium was air. The stripping medium was water vapor. In the primary reaction zone, the average reaction temperature was 450° C.; the gauge pressure was 0.1 MPa; and the gas linear speed was 1.25 m/s. In the first riser reactor, the average temperature was 558° C.; the gauge pressure was 0.1 MPa; and the gas linear speed was 5.0 m/s. In the second riser reactor, the average temperature was 550° C.; the gauge pressure was 0.1 MPa; and the gas linear speed was 5.7 m/s. At the lower portion of the primary reaction zone, the feedstock was methanol having a purity of 99.5% with a feed rate of 2 kg/h; the catalyst was SAPO-34. At the lower portion of the first riser reactor, the feedstock was the mixed C4 olefins containing olefins in an amount of 88% by weight and fed at a feed rate of 0.54 kg/h. Meanwhile, water vapor was added into the feedstock at the lower portion of the riser reaction zones as the diluent. The weight ratio of water vapor to the mixed C4 olefins was 1:1. The feedstock at the lower portion of the second riser reactor was the light hydrocarbons having an ethylene mass content of 47%, which also comprised methane 9%, ethane 12%, propane 22%, and the balance being hydrogen, CO, $CO_2$ and the like, wherein the total amount of all components is 100%. The regenerated catalyst recycling from the first regeneration zone to the primary reaction zone had an amount of carbon deposited thereon in a mass fraction of 1.25%; the regenerated catalyst fed from the second regeneration zone to the reactor of two risers had an amount of carbon deposited thereon in a mass fraction of 0.27%. The first regeneration zone had a temperature of 648° C.; the second regeneration zone had a temperature of 677° C. For the regenerated catalyst in the first regeneration zone, 50% by weight was fed into the second regeneration zone; 50% by weight was recycled into the primary reaction zone. For the regenerated catalyst in the second regeneration zone, 30% by weight was fed into the first riser reactor; 70% by weight was fed into the second riser reactor. While maintaining the flow control stability of the catalyst, the product from the outlet of the reactor was subjected to online gas chromatography. In the product stream I, the yield of light olefins (carbon basis) reached 80.19% by weight, while in the product streams II and III, the yield of light olefins reached 41.25% by weight.

EXAMPLE 2

The conditions as set forth in Example 1 were followed. In the primary reaction zone, the average reaction temperature was 400° C.; the gauge pressure was 0.01 MPa; and the gas linear speed was 2.0 m/s. In the first riser reactor, the average temperature was 510° C.; the gauge pressure was 0.01 MPa; and the gas linear speed was 10.0 m/s. In the second riser reactor, the average temperature was 500° C.; the gauge pressure was 0.01 MPa; and the gas linear speed was 10.0 m/s. At the lower portion of the primary reaction zone, the feedstock was methanol having a purity of 99.5% with a feed rate of 1.74 kg/h; the catalyst was SAPO-34. At the lower portion of the first riser reactor, the feedstock was mixed C4 olefins containing olefins in an amount of 88% by weight and fed at a feed rate of 0.24 kg/h. Meanwhile, water vapor was added into the feedstock at the lower portion of the riser reaction zones as the diluent. The weight ratio of water vapor to the mixed C4 olefins was 1:1. The feedstock at the lower portion of the second riser reactor was the light hydrocarbons having an ethylene mass content of 47%, which also comprised methane 9%, ethane 12%, propane 22%, the balance being hydrogen, CO, $CO_2$ and the like, wherein the total amount of all components is 100%. The regenerated catalyst recycling from the first regeneration zone to the primary reaction zone had an amount of carbon deposited thereon in a mass fraction of 0.5%; the regenerated catalyst fed from the second regeneration zone to the reactor of two risers had an amount of carbon deposited thereon in a mass fraction of 0.16%. For the regenerated catalyst in the first regeneration zone, 80% by weight was fed into the second regeneration zone; 20% by weight was recycled into the primary reaction zone. For the regenerated catalyst in the second regeneration zone, 70% by weight was fed into the first riser reactor; 30% by weight was fed into the second riser reactor. While maintaining the flow control stability of the catalyst, the product from the outlet of the reactor was subjected to online gas chromatography. In the product stream I, the yield of light olefins (carbon basis) reached 77.97% by weight, while in the product streams II and III, the yield of light olefins reached 38.45% by weight.

EXAMPLE 3

The conditions as set forth in Example 1 were followed. In the primary reaction zone, the average reaction temperature was 500° C.; the gauge pressure was 0.3 MPa; and the gas linear speed was 0.8 m/s. In the first riser reactor, the average temperature was 650° C.; the gauge pressure was 0.3 MPa; and the gas linear speed was 3.0 m/s. In the second riser reactor, the average temperature was 630° C.; the gauge pressure was 0.3 MPa; and the gas linear speed was 3.0 m/s. At the lower portion of the primary reaction zone, the feedstock was methanol having a purity of 99.5% with a feed rate of 2.96 kg/h; the catalyst was SAPO-34. At the lower portion of the first riser reactor, the feedstock was mixed C4 olefins containing olefins in an amount of 61% by weight and fed at a feed rate of 0.67 kg/h. Meanwhile, water vapor was added into the feedstock at the lower portion of the riser reaction zones as the diluent. The weight ratio of water vapor to the mixed C4 olefins was 1:1. The feedstock at the lower portion of the second riser reactor was the light hydrocarbons having an ethylene mass content of 31%, which also comprised methane 10.2%, ethane 18%, propane 27%, the balance 13.8% being hydrogen, CO, $CO_2$ and the like. The regenerated catalyst recycling from the first regeneration zone to the primary reaction zone had an amount of carbon deposited thereon in a mass fraction of 2.0%; the regenerated catalyst fed from the second regeneration zone to the reactor of two risers had an amount of carbon deposited thereon in a mass fraction of 0.5%. While maintaining the flow control stability of the catalyst, the product from the outlet of the reactor was subjected to online gas chromatography. In the product stream I, the yield of light olefins (carbon basis) reached 76.28% by weight, while in the product streams II and III, the yield of light olefins reached 35.22% by weight.

EXAMPLE 4

The conditions as set forth in Example 1 were followed, except for the type of the molecular sieves in the catalyst. The test results are reported in Table 1.

TABLE 1

| Parameters | Molecular Sieve Type | Yield of light olefin in the product stream I (carbon basis), % by weight | Yield of light olefin in the product streams II and III, % by weight |
|---|---|---|---|
| Example 4 | SAPO-18 | 78.24 | 37.56 |
| Example 5 | SAPO-56 | 65.39 | 21.89 |
| Example 6 | mixture of SAPO-34 and SAPO-18 (wherein the weight ratio of SAPO-34:SAPO-18 is 2:1) | 79.65 | 39.47 |

What is claimed is:

1. A process for producing at least one light olefin, comprising:

(1) providing a reaction-regeneration system comprising a primary reaction zone, a secondary reaction zone, and a regenerator, wherein the secondary reaction zone comprises two or more risers; and the regenerator comprises two or more regeneration zones;

(2) transporting a first raw material into the primary reaction zone to be contacted with at least one catalyst comprising at least one molecular sieve, producing a product stream I, and also forming at least one coked catalyst, wherein the amount of carbon deposited on the coked catalyst ranges from about 1% to about 6% by mass;

(3) transporting said at least one coked catalyst to a first regeneration zone of the regenerator for regeneration, transporting from about 50% to about 80% by weight of the resulting regenerated catalyst to the second regeneration zone, and recycling from about 20% to about 50% by weight of the resulting regenerated catalyst to the primary reaction zone, wherein the amount of carbon deposited on the catalyst recycled from the first regeneration zone to the primary reaction zone ranges from about 0.5% to about 2.0% by mass;

(4) transporting at least one portion of the regenerated catalyst in the second regeneration zone to the first riser of the secondary reaction zone to be contacted with a second raw material, thus producing a product stream II, transporting another portion of the regenerated catalyst into the second riser of the secondary reaction zone to be contacted with a third raw material, thus producing a product stream III, wherein the amount of carbon deposited on the catalyst fed into the first or second riser is less than about 0.5% by mass; and (5) transporting both the product streams II and III and the catalyst into a secondary disengaging zone, subjecting the product streams II and III to gas-solid separation and further transporting the result thereof into a separation section, and recycling the separated catalyst to the first regeneration zone of the regenerator;

wherein:

the first raw material comprises methanol;

the second raw material comprises a mixed heavy hydrocarbon having a carbon number of 4 or more and an olefin mass content of more than about 60% by weight relative to the total weight of the second raw material, and/or a mixed hydrocarbon having a carbon number of 4 or more obtained from said separation section; and the third raw material comprises a light hydrocarbon having an ethylene mass content of more than about 30% by weight relative to the total weight of the third raw material, and/or a light hydrocarbon obtained from said separation section.

2. The process according to claim 1, wherein said primary reaction zone is a fast fluidized bed.

3. The process according to claim 1, wherein the at least one molecular sieve is chosen from SAPO-5, SAPO-11, SAPO-17, SAPO-18, SAPO-34, SAPO-35, SAPO-44 and SAPO-56.

4. The process according to claim 3, wherein the at least one molecular sieve is SAPO-34.

5. The process according to claim 1, wherein a stripping section is arranged at the lower portion of said secondary disengaging zone.

6. The process according to claim 1, wherein said primary reaction zone has a reaction temperature ranging from about 400° C. to about 500° C., a gauge pressure ranging from about 0.01 MPa to about 0.3 MPa, and a gas linear speed of from about 0.8 m/s to about 2.0 m/s.

7. The process according to claim 1, wherein the first riser reactor has a reaction temperature ranging from about 510° C. to about 650° C., a gauge pressure ranging from about 0.01 MPa to about 0.3 MPa, and a gas linear speed ranging from about 3.0 m/s to about 10.0 m/s.

8. The process according to claim 1, wherein the second riser reactor has a reaction temperature ranging from about 500° C. to about 630° C., a gauge pressure ranging from about 0.01 MPa to about 0.3 MPa, and a gas linear speed ranging from about 3.0 m/s to about 10.0 m/s.

9. The process according to claim 1, wherein from about 30% to about 70% by weight of the regenerated catalyst in said second regeneration zone is fed into the first riser reactor, while from about 30% to about 70% by weight of the regenerated catalyst in said second regeneration zone is fed into the second riser reactor, said weights being relative to the total weight of the regenerated catalyst in said second regeneration zone.

* * * * *